United States Patent [19]

McLeroy

[11] Patent Number: 5,408,893

[45] Date of Patent: Apr. 25, 1995

[54] GROUND MOISTURE PROBE

[76] Inventor: David E. McLeroy, 10295 Byrne Ave., Cupertino, Calif. 95014

[21] Appl. No.: 141,773

[22] Filed: Oct. 25, 1993

[51] Int. Cl.$^6$ .............................................. G01N 1/08
[52] U.S. Cl. ............................... 73/864.44; 73/864.45; 73/864.51; 73/864.64; 175/20
[58] Field of Search .......... 73/864.44, 864.45, 864.51, 73/864.64; 175/20

[56] References Cited

U.S. PATENT DOCUMENTS

| | | |
|---|---|---|
| 141,998 | 8/1873 | Clark . |
| 513,789 | 1/1894 | Horst . |
| 2,544,728 | 3/1951 | Safford .............................. 73/425.2 |
| 3,273,930 | 9/1966 | Gottfried .......................... 73/864.44 |
| 4,177,896 | 10/1978 | Weber .................................. 175/84 |
| 4,252,200 | 2/1981 | Peterson ............................... 175/20 |
| 4,442,721 | 4/1984 | Singer ............................. 73/864.51 |
| 4,556,114 | 12/1985 | Ryan .................................... 175/20 |
| 5,121,643 | 6/1992 | Voloudakis ...................... 73/864.41 |

Primary Examiner—Richard E. Chilcot, Jr.
Assistant Examiner—Max H. Noori
Attorney, Agent, or Firm—Skjerven, Morrill, MacPherson, Franklin & Friel

[57] ABSTRACT

A ground soil moisture probe is constructed of a solid cylindrical rod with a solid soil-piercing bottom conical tip end an inverse conic section hard facing protuberance extending from above the rod tip end and fairing into the rod tip end. A tangential slot extends thereabove, forming with a flat stop of the protuberance a soil-collection and soil-holding shelf. The probe is inserted into the soil or sod being moisture tested to a predetermined depth, controlled by a depth-adjustable circular depth stop extending from the rod. The sample is obtained by a scraping action of the shelf outer edge on the sides of the hole made by insertion of the probe. A finger pinch test is described where a lop-sided sample ball of soil is pinched from the shelf and the general comparative amount of moisture in the sample determined by the feel and appearance of the soil sample to the operator.

8 Claims, 2 Drawing Sheets

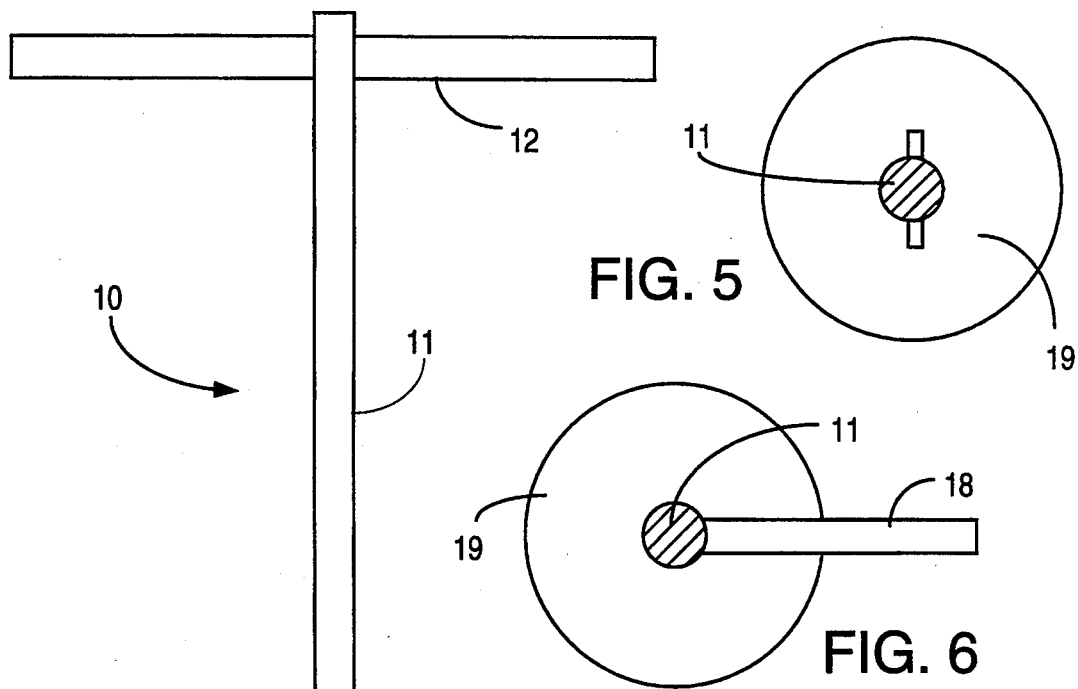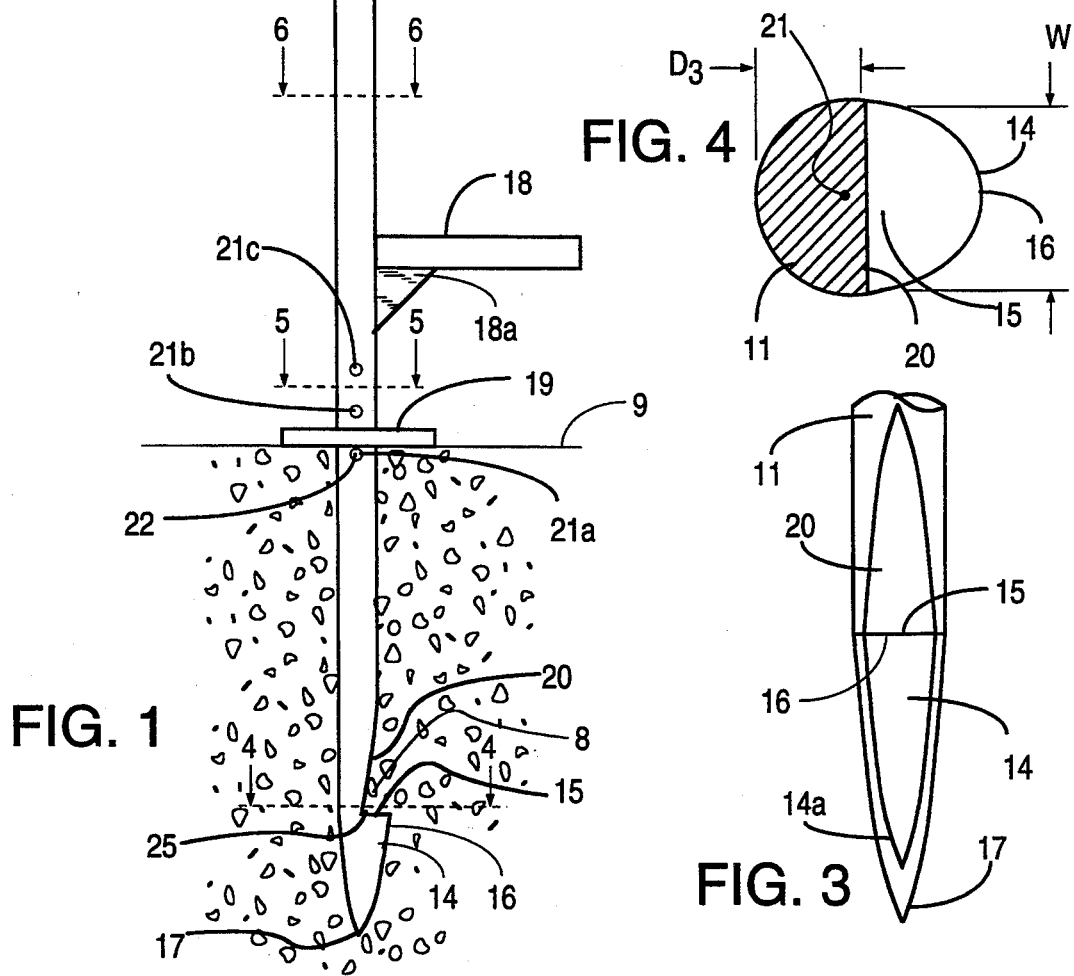

GROUND MOISTURE PROBE

BACKGROUND OF THE INVENTION

1. Field of the Invention

This invention pertains to a ground moisture probe. More particularly, the invention is directed to a ground-insertable probe for obtaining a soil sample at a predetermined ground depth which sample can be easily and quickly accessed for making a relatively instant general moisture content determination.

2. Material Art

Heretofore rather sophisticated dielectric capacitance probes using micro processor sensors or conventional coring tools have been employed to directly measure or to obtain a core sample for sensing moisture. The latter generally are comprised of a hollow tube having a bottom circular edge which is foot-pressed into the ground or sod to pierce the ground which forces a 20-25 cm long soil core into its interior during a downward push of the probe. The tool is then removed and the soil core exposed in an elongated window in the tool sidewall. Difficulties are encountered when the circular edge strikes a rock in the ground or sod and sharpness of the edge is quickly diminished. Further, there is a degree of difficulty in accessing the core sample. U.S. Pat. No. 4,117,896 illustrates this type of core sampler. U.S. Pat. No. 2,544,728 illustrates a scoop-like scraper which is positionable in a string to scrape minerals from the sides of a drilled hole H. U.S. Pat. No. 4,252,200 shows a probe for obtaining a plurality of samples from placer deposits when the probe is hollow with a plurality of side windows with edge teeth. After the probe is pushed into the deposits the probe shaft is rotated exposing the windows which allow entry of the deposits into the probe. The shaft is rotated to close the windows and the probe is withdrawn. U.S. Pat. No. 5,121,643 is directed to a tool comprising a cylindrical rod with a chisel end and a plurality of collecting pockets extending tangentially into the rod and serially along the rod periphery, the first pocket being appreciably above the chisel end. The pockets are 9/37" in diameter and thus would be difficult to finger-access the pocket for easy sample removal. Further, due to such dimension not enough soil is available in a pocket to conduct a feel and moisture appearance estimate. After tool insertion, the tool is twisted to force samples into each pocket and the tool is removed. Borers for other purposes which employ a sharp pointed end are seen in U.S. 513,789 directed to a hop trier and U.S. 141,998 a borer for sampling cotton. Each are designed to sample the interior of a bale by piercing the bale cloth and grabbing a sample by twisting.

SUMMARY OF THE INVENTION

A particular need for a simple, reliable and quick probe for moisture mapping a lawn or landscape area has arisen due to the need to conserve water in drought-stricken states and other locations with little natural rainfall. Such mapping also indicates the efficiency and distribution of irrigation water for the upkeep of grass, lawns, trees and scrubs. One cannot tell the moisture at a plant's root area by looking at the plant surface. A macro determination of soil moisture, particularly accompanied by computer modeling, will aid in determining the spacing, throw, timing, frequency and valving of sprinkler devices over a wide surface area. The result is a system for capturing and improving the health of the landscaping while conserving the utilization of irrigation water.

The probe of this invention includes a solid cylindrical rod and a solid bottom protuberance of hard facing steel, extending above a solid conically pointed soil or sod—piercing tip. The protuberance is preferably formed by a weldment of hard facing steel welded to the bottom of cylindrical rod just above the soil-piercing rod tip and by machining or grinding a longitudinal tapered slot in the probe rod just above the rod tip. This leaves a flat shelf or ledge extending outwardly beyond the diameter of the cylindrical rod and forms with a ground or machined part of the weldment and the slot a soil-holding and soil-collection shelf volume. The slot is relatively shallow so as to retain a maximum cross-section of the rod over its entire length above the pointed tip so as to prevent bending of the rod by soil insertion forces. When the rod is vertically pushed down into the soil, the sides of the hole made by the rod are slightly compressed such that little or no soil fills the shelf volume when the probe arrives at its predetermined depth. When the probe is vertically pulled up, the outer periphery of the ledge scrapes a sample off a side of the insertion hole immediately above the shelf volume, filling and packing a soil sample in that volume from that insertion depth until the volume is filled. As the rod proceeds upwardly, the filled sample is smoothed.

Upon removal of the probe from the soil, and the probe lifted, generally to a horizontal position, the user's thumb and index finger can easily access the shelf volume to "pinch" and remove a recovered approximately 1.3 cm lop-sided sample ball of soil to proximately determine, by feel and appearance, the general comparative amount of moisture in the sample i.e. dry, slightly moist, average moisture, soil is wet or soil is saturated. A range of % moisture can be determined by the finger pinch test. The invention also includes, if desired, various stop positions on the rod to enable setting of a desired probe depth into the soil. A skilled operator can also judge probe depth generally to about one centimeter accuracy by determining how close the soil surface is to the underside of a footpad incorporated on the probe.

BRIEF DESCRIPTION OF THE DRAWING

FIG. 1 is a side view of the preferred embodiment of the invention shown in an insertion position in a soil cross-section.

FIG. 3 is a front view thereof.

FIG. 4 is a cross-sectional view taken on the line 4—4 of FIG. 1.

FIG. 5 is a cross-sectional view taken on the line 5—5 of FIG. 1.

FIG. 6 is a cross-sectional view taken on the line 6—6 of FIG. 1.

DETAILED DESCRIPTION

Figure 2:
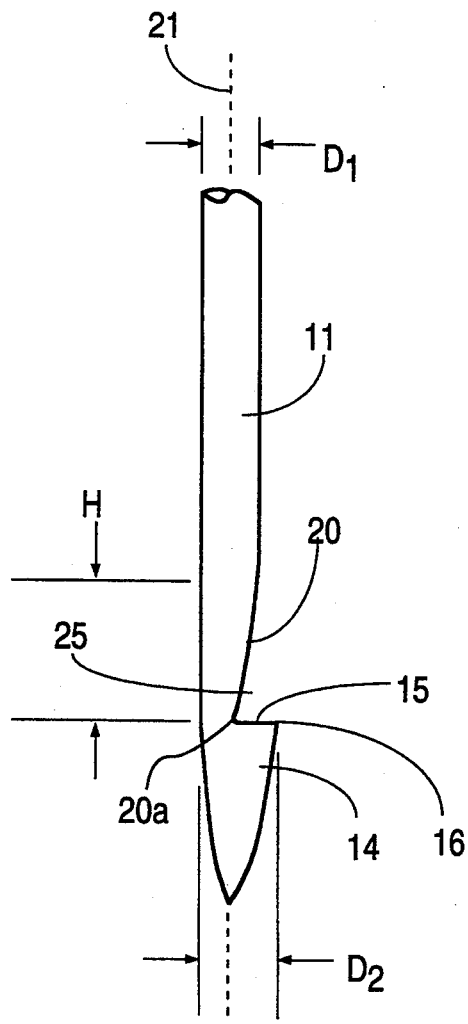
FIG. 2 is a detailed side view of the probe protuberance and soil-holding shelf.

FIG. 1 shows the ground moisture probe 10 of the invention which includes a solid cylindrical metal rod 11 of 1020 hot-rolled or cold-rolled steel of about 1.27 cm diameter. Rod 11 includes a solid pointed soil or sod-piercing tip 17 and a solid bottom protuberance 14 immediately thereabove. A machined or ground transverse generally triangular slot 20 extends immediately above the protuberance 14 forming a flat shelf 15 extending from the rod interior outwardly to the outer periphery of rod 11 and to an extending shelf outer edge 16 as best seen in FIG. 4. The protuberance 14 generally is formed by placement of a substantially generally of about one-half an inverted cone weldment of steel hard-facing metal such as Stoody hard-facing weld rod #35 (as used also on backhoe bucket teeth) on the rod periphery. The protuberance extends over a cylindrical outer arc surface of the rod of from about 170° to about 190°, preferably about 180°, and forms an inverse conic section bottom surface 14a faired into tip 17 and having an axis spaced from and parallel to the axis 21 (FIG. 2) of the cylindrical rod. The flat shelf 15 with the tapered slot 20 forms a soil-holding and soil-collection volume 25 which is filled with a soil sample 30 (FIG. 7) when the rod 11 pulled from soil 8 (FIG. 1) from a position below soil ground surface 9.

A foot pad 18 of square rod, including an angled web support 18a is welded to the rod 11 allowing a user's foot to downwardly press on the foot pad and apply a leg force to augment the user pushing on a cross-piece handle 12 to insert the rod vertically into the soil. A depth stop 19 in the form of a ring washer or peg may surround rod 11 transversely to allow downward movement of probe 10 to a desired depth of soil penetration. A user may also merely judge the depth from the observed distance of the underside of the foot pad to the ground surface 9 which gives a general known depth of insertion or within a centimeter or so. The stop 19 may be adjustable vertically by providing a series of transverse apertures 21a, 21b, 21c in the rod 11 into which metal or plastic pins 22 can be inserted at various levels so that the washer 19 is confined between any two apertures e.g. 21a and 21b or 21b and 21c, and the pins extending therethrough. In FIG. 1, pin 22 will be forced a slight distance into the soil 8 until further downward movement of the probe allows the pin in aperture 21b to contact stop 19 and press the stop in compression against the soil surface 9 preventing further soil penetration of the probe.

The probe is fully inserted to the desired depth by the hand and foot force of the operator. The probe is then vertically withdrawn from the soil the ledge and outer edge 16 scraping a soil sample from immediately above the fully inserted position into the shelf volume 25. With use of the operator's thumb and index finger a "pinch" of soil sample is easily removed from shelf 15 due to the relatively unobstructed opening and held in the fingers or hand as a lop-sided mass or ball of soil. The operator then proximately determines subjectively by feel and appearance, the general comparative amount of moisture in the sample i.e. dry (about 0 to 25%); slightly moist (about 25-50%); average moisture (about 50-75%); wet (about 75-95%); or saturated (about 95-100%). This is an accepted test method set forth in a guide entitled "Estimating Soil Moisture by Feel and Appearance" published by the Soil Conservation Service of the United States Department of Agriculture. An operator is trained by feeling various samples of known moisture and noting the viability, color, stickiness, finger staining, slickness, ribbon-forming, free-water and breaking-up characteristics of the soil ball.

As seen in FIG. 2, 3 and 4, the tapered slot 20 is relatively shallow being less at its greatest depth (not counting the protuberance 14) than one-half the diameter $D_1$ of the rod 11 thus leaving a minimum rod thickness $D_3$ just greater than one-half the full initial diameter of the rod 11. This retains a maximum cross-section of the rod over its entire length above the pointed tip 17 so as to prevent bending of the rod due to soil insertion forces. The vertical longitudinal axis 21 of rod 11 (FIG. 2) is thus not intersected by slot 20. The slot 20 preferably includes a deepened lower end 20a which aids in holding the soil sample in volume 25. The shelf 15 extends outwardly to an outer edge 16 forming an increased diameter $D_2$ (FIG. 2) of the rod 11 at the protuberance. The preferred maximum width W of the slot 20 bottom is typically 0.95 cm The depth of the slot ($D_2$-$D_3$ at edge 16) is typically 0.64 cm The height H of the slot is typically 6.3 cm. The height of the slot is in the range of from 8 to 12 times the depth of the slot.

FIGS. 5 and 6 show the plan footprint of the depth stop 19 with pin 22 and the foot pad, respectively. A closer vertical spacing of pins 22 may be provided so that the penetration of the bottom pin into the soil surface is minimized. Pins 22 are force-fit into and have ends extending outwardly equally from apertures 21a et al. Pins 22 have a length approximately the same as the diameter of the depth stop washer 19.

Figure 7:
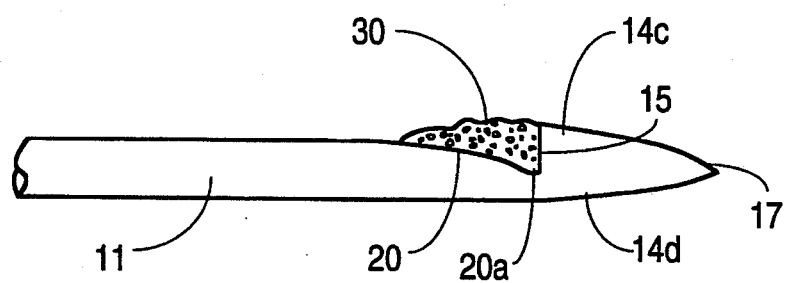
FIG. 7 is a side view of the probe bottom in horizontal position showing a withdrawn soil sample on the soil shelf.

FIG. 7 illustrates an actual soil sample 30 contained in volume 25 and confined therein by the packing of the sample between the shelf 15, slot 20 and deepened lower end 20a. As can be seen, the sample can be easily pushed off the shelf laterally from either side of the shelf into the operator's hand or fingers. Surfaces 14c and 14d denote compoundly curved ground surfaces extending from the shelf side to the tip 17.

In a commercial version the probe has a total length of 89 cm, the rod 11 is 1.27 cm in diameter, the handle 12 is a cylindrical rod 2.2 cm in diameter and 24 cm long; the foot pad 18 is 11 cm long, 1.3 wide and 32 cm above the tip 17. The distance from the ledge 15 to the tip 17 is 3 cm.

The above description of embodiments of this invention is intended to be illustrative and not limiting. Other embodiments of this invention will be obvious to those skilled in the art in view of the above disclosure.

I claim:

1. A soil moisture probe comprising a solid cylindrical rod having a sharp soil-insertable tip end, an opposite handle end and a longitudinal fixed diameter intermediate portion sized to be inserted into soil;
   an insertion handle extending from the handle end;
   an integral protuberance extending outwardly from a cylindrical outer arc surface of said rod adjacent to said soil-insertable tip end, said protuberance having an upper generally flat surface forming a shelf extending outwardly beyond the diameter of said fixed diameter intermediate portion, and a fairing extending from said shelf to said tip end; and
   a longitudinally tapered slot extending from said shelf and merging with said fixed diameter intermediate portion.

2. The moisture probe of claim 1 in which said cylindrical outer arc surface extends from about 170° to about 190°.

3. The moisture probe of claim 2 in which said cylindrical outer arc is about 180°.

4. A soil moisture probe comprising a solid cylindrical rod having a sharp soil-insertable tip end and an opposite handle end;
   an insertion handle extending from the handle end;
      an integral protuberance extending outwardly from a cylindrical outer arc surface of said rod adjacent to said soil-insertable tip end, said protuberance having an upper generally flat surface; and
   a fairing extending from said shelf to said tip end; and wherein said fairing has an axis spaced from and parallel to a central axis of the cylindrical rod.

5. The moisture probe of claim 1 wherein the height of said tapered slot along a longitudinal length of said rod is from 8 to 12 times the depth of said slot at said shelf, said depth being less than one-half of the fixed diameter of the intermediate portion.

6. The moisture probe of claim 1 further including a depth stop extending transversely from said rod below said handle and above said protuberance at a distance from said protuberance representing a desired depth of soil penetration of the probe; and
   including means on said rod for adjusting the position of said depth stop on said rod.

7. The moisture probe of claim 1 including a foot pad extending from said rod above said protuberance at a distance greater than an intended soil-insertion depth, for foot-forcing the probe into the soil.

8. A soil moisture probe comprising a solid cylindrical rod having a sharp soil-insertable tip end and an opposite handle end;
   an insertion handle extending from the handle end;
      an integral protuberance extending outwardly from a cylindrical outer arc surface of said rod adjacent to said soil-insertable tip end, said protuberance having an upper generally flat surface; and
   wherein said protuberance is a ground hard facing weldment extending from said rod.

* * * * *